United States Patent [19]

Alexanian et al.

[11] 4,379,767

[45] Apr. 12, 1983

[54] MANUFACTURE OF ISOCYANATES

[75] Inventors: Vazken A. Alexanian, Darien; Peter S. Forgione, Stamford; Laurence W. Chang, Orange, all of Conn.

[73] Assignee: American Cyanamid Company, Stamford, Conn.

[21] Appl. No.: 355,825

[22] Filed: Mar. 8, 1982

[51] Int. Cl.³ .................. C07C 118/00; C07C 125/03
[52] U.S. Cl. ............................. 260/453 P; 260/544 C
[58] Field of Search ..................................... 260/453 P

[56] References Cited

U.S. PATENT DOCUMENTS 3,290,350  12/1966  Hoover ........................... 260/453 P
4,130,577  12/1978  Nagato et al. ................... 260/453 P

*Primary Examiner*—Dolph H. Torrence
*Attorney, Agent, or Firm*—Steven J. Hultquist

[57] ABSTRACT

A process for the production of tertiary benzyl isocyanates by reaction of the corresponding olefin with a carbamoyl halide to form the benzyl halide followed by the reaction of the benzyl halide with an excess of isocyanic acid to form the isocyanate and carbamoyl halide which can be recovered and recycled.

11 Claims, No Drawings

MANUFACTURE OF ISOCYANATES

This invention relates to the manufacture of tertiary benzylic isocyanates, particularly isocyanates such as tetramethylxylylenenediisocyanates (TMXDI) and isopropenyldimethylbenzyl isocyanates (TMI), and in particular provides a process for the the preparation of such isocyanates from the corresponding olefins and isocyanic acid (HNCO).

Isocyanates are a well known and a valuable class of compounds. In particular meta-and para-TMXDI are useful for reaction with a wide variety of polyols to give polyurethanes which are either rigid or flexible and which can be endowed with a wide variety of properties. Thus such polyurethanes can be formed into rigid and foamed articles, sheets, high-density sheets, and articles of various shapes. The light stability of polyurethanes makes them extremely useful in coatings and other applications where light stability is desirable, e.g. light stable RIM elastomers.

Tertiary benzylic isocyanates, such as TMXDI, have heretofore been manufactured by phosgenation of the corresponding organic amines, by reaction of the corresponding olefins with isocyanic acid (U.S. Pat. No. 3,290,350), by reaction of the corresponding aromatic halides with an alkali metal isocyanate (U.S. Pat. No. 4,130,577), and by reaction of the corresponding aromatic halides with isocyanic acid (copending application Ser. No. 331,696, filed Dec. 17, 1981 now U.S. Pat. No. 4,361,518, by Balwant Singh and William A. Henderson Jr.).

The phosgenation route suffers disadvantages from the commercial standpoint in that phosgene itself is an unsafe material and difficult to handle. In addition the organic amines are difficult to produce. The olefin addition route suffers the disadvantages that the yields are poor and that large amounts of olefin and isocyanic acid are lost through self polymerization. On the other hand while the reaction of the halide with the alkali metal isocyanate can provide high yields, the reaction times are long, and the halogen is completely lost as the alkali metal halide, recoverable only at great expense. The reaction of the halide with isocyanic acid is a substantial improvement in terms of yield and reaction time over the prior processes but consumes hydrogen halide in the manufacture of the aromatic halides from the corresponding olefins.

It is thus an important object of this invention to utilize the reaction of aromatic halide and isocyanic acid in the manufacture of tertiary benzylic isocyanates, in a way which only involves a net consumption of isocyanic acid and the corresponding olefin.

In accordance with this invention the relative high yields and fast reaction times of the reaction of the halide with isocyanic acid to introduce the isocyanato moiety are taken advantage of. The reaction of olefin with hydrogen chloride to produce the aromatic halide and loss of chloride in the process are avoided by introducing the halogen atom into the olefin by the reaction with carbamoyl halide to form the tertiary benzylic halide and isocyanic acid which are then reacted with additional isocyanic acid to convert to the desired isocyanate. Carbamoyl halide is produced as a byproduct which is then recycled to react with the olefin.

The reaction is carried out in a solvent medium for the olefin, isocyanic acid, resulting aromatic halide and finally the resulting isocyanate. Typical solvents are aromatic hydrocarbons, halogenated hydrocarbons and aliphatic hydrocarbons such as toluene, xylene, chlorobenzene or dichlorobenzene, heptane, benzene, methylene chloride and like. Generally, the solvent is an aprotic or non-polar solvent. Both the reaction of carbamoyl halide and olefin and the reaction of the resulting aromatic halide and isocyanic acid proceed at relatively low temperatures, almost instantaneously in the presence of suitable catalyst. The reactions proceed, however somewhat more slowly, even in the total absence of catalyst. In either event the reactions are preferably carried out at temperatures on the order of $-10°$ to $10°$ C. Higher and lower temperatures can be utilized. Higher temperatures, however, favor polymerization of isocyanic acid to form solids while lower temperatures reduce the speed of reaction.

The reactants should be substantially anhydrous. Small amounts of water above approximately 700 ppm tend to make the reaction sluggish.

Tertiary benzyl olefins which can be reacted with carbamoyl halide and then with isocyanic acid to produce tertiary benzyl isocyanates in accordance with this invention are characterized by a tertiary carbon attached to the aromatic nucleus and include such compounds as diisopropenyl benzene (DIPEB), mixed diisopropenyl naphthalenes and the like. The aromatic moiety, which can be a single or fused ring structure, can have other non-reactive substituents such as alkyl and alkoxy substituents as well as halogens such as chlorine, bromine and flourine, and certain non-reactive halo-substituted alkyls, e.g., $CF_3$. In general the starting olefins are described in the generalized formula

in which: $R_1$ is an alkylidene group having from 1 to 3 carbon atoms, $R_2$ is an alkyl group having from 1 to 3 carbon atoms, and $R_3$ is an aromatic hydrocarbon group such as phenyl, biphenyl, or naphthyl, or such an aromatic hydrocarbon group having substituents such as halogen atoms, methyl or methoxy groups or substituents of the formula

The preferred catalysts are zinc chloride, zinc bromide and zinc idodide. Other Lewis acids, such as bismuth trichloride and bismuth tribromide exhibit activity. Ferric chloride and stannous chloride have weak catalytic activity, while boron trichloride, mercuric chloride, aluminum tribromide, aluminum trichloride, ferrous chloride, zirconium chloride, and cuprous chloride exhibit little or no catalytic activity. Other zinc catalysts which are effective in the process of this invention are zinc neodecanoate, zinc fluoride and zinc dodecylbenzenesulfonate.

The catalyst can be added in solid form, or it can be slurried in a suitable diluent or dissolved in a suitable solvent, such as diethyl ether, diisobutyl ketone, 2-octanone and isobutyl butyrate, and added to the reaction mixture. Preferably the catalyst is added in solution form. Basic solvents, such as pyridine, are to be avoided as the isocyanic acid is almost completely lost in polymerization to solids.

The reaction of the aromatic olefin with carbamoyl halide is more complete when approximately 20 to 50% excess of carbamoyl halide is used than when the reaction is with an equivalent amount. The presence of excess carbamoyl halide has no deleterious effect on the zinc catalyzed reaction of the halides with isocyanic acid at such as excess of carbamoyl halide; but as the excess of carbamoyl halide increases to 200 to 400% lower yields of the isocyanates are obtained.

For a more complete understanding of the practical application of this invention, reference is made to the following examples.

EXAMPLE I 0.73 grams of dry hydrogen chloride (0.020 mole) was introduced into a solution of 0.86 g. isocyanic acid (0.020 mole) in 3.44 g. toluene at 0° under a nitrogen atmosphere. 1.58 g. of p-DIPEB (0.010 mole) were slowly introduced to the resultant carbamoyl chloride solution over a period of ten minutes with stirring while maintaining the temperature at 0° C. After fifteen minutes tetramethyl-p-xylylene dichloride (p-TMXDC) was present in 80% yield. 23 ml of 20.4% isocyanic acid in toluene (0.100 mole) was added at 0° C. followed by addition of 0.50 ml of 1M zinc chloride (0.00050 mole) in ether over a period of 2 minutes at 0° C. After one hour p-TMXDI had formed in 63% yield based on the DIPEB.

EXAMPLE II 1.58 g. (0.010 mole) of m-DIPEB was added to a suspension of 1.749 g. (0.022 mole) of carbamoyl chloride in toluene over a period of ten minutes at 0° C. with stirring to give m-TMXDC. Further treatment with isocyanic acid and zinc chloride as in Example I gave m-TMXDI in 78% yield based on the starting olefin.

EXAMPLE III 2.48 grams (0.020 mole) of carbamoyl bromide was prepared following the procedure of Example I with the substitution of hydrogen bromide for hydrogen chloride. 1.58 g (0.010 mole) of m-DIPEB were then added along with isocyanic acid (0.100 mole) and zinc chloride (0.00050 mole) in ether as in Example I. After 30 minutes a mixture consisting of 13% tetramethyl-m-xylylene dibromide, 43% of the monoisocyanate-monobromide and 38% of m-TMXDI was obtained.

EXAMPLE IV 2.48 parts by weight (0.020 mole) of carbamoyl bromide were prepared as in Example III followed by the addition of m-DIPEB (1.48 parts by weight, 0.010 mole). No catalyst was added. 0.100 mole of isocyanate acid in toluene was added stirring at room temperature for 3 hours. The resultant mixture contained less than 1% of the dibromide, 15% of the monoisocyanate-mono-bromide and 68% of the desired m-TMXDI.

EXAMPLE V

The carbamoyl chloride formed in Example I was effectively recycled without removal of zinc chloride from the reaction mixture by adding more diisopropenyl benzene to the reaction mixture as shown in Table I. After 60 minutes the reaction mass contained 9% TMI and 63% p-TMXDI. At that time 0.010 moles of p-DIPEB and 0.020 moles of isocyanic acid were added to the reaction mixture. Conversion at 150 minutes is shown in Table I. At that time additional zinc etherate (0.00050 moles) was added with further conversion as shown in Table I. In Table I the yields are shown as percentages of p-DIPEB.

TABLE I

| | Recycle of NH$_2$COCl Without Removal of ZnCl$_2$ | | | | |
|---|---|---|---|---|---|
| | Time (min.) | % p-TMXDC | % p-TMI | % p-TMXDI | % Total Organics |
| End of Cycle I | 60 | 0 | 9 | 63 | 72 |
| 1 equiv. p-DIPEB + 1 equiv. HNCO added at 60 min | 150 | 54 | 24 | 75 | 153 |
| ZnCl$_2$-ether added at 150 min. | 165 | 6 | 35 | 89 | 130 |

An important facet of this invention is the recovery of the carbamoyl chloride from the reaction mixture after the production of the diisocyanates. Excess isocyanic acid also is recoverable, as shown in the following example.

EXAMPLE VI

A solution containing 25 ml. of 20.0% isocyanic acid (0.010 mole), 3.06 grams of carbamoyl chloride (0.038 mole) and 55 ml. of toluene was distilled at room temperature under 25 mm. Hg pressure for 2.5 hours. The distillate was collected in a dry ice-acetone cold trap. Analyses of the mixture collected in the cold trap by reaction of sodium hydroxide to give sodium isocyanate and sodium chloride showed that 92% of the isocyanic acid and 96% of the carbamoyl chloride had been recovered.

EXAMPLE VII

The distillation process is applicable to the separation of carbamoyl chloride and isocyanic acid for recycle from reaction mixtures. A typical reaction mixture containing p-TMXDI, p-TMI, zinc chloride etherate catalyst, carbamoyl chloride, unreacted p-TMXDC and isocyanic acid in toluene was filtered through a column filled with sand to remove solids formed during the reaction. The filtrate was then distilled at room temperature under 25 mm. Hg for 3 hours and collected in a dry ice-acetone cold trap. The distillate was treated with aqueous sodium hydroxide solution and analyzed for chloride and sodium isocyanate. The analysis showed that 99% of the theoretical amount of carbamoyl chloride formed in the reaction mixture and 56% of the isocyanic acid had been recovered for recycle.

EXAMPLE VIII

A continuous, backstirred reactor is set up with provision for separate addition of para-diisopropenyl benzene in toluene solution and of isocyanic acid/carbamoyl chloride in toluene solution. The reactor is provided with agitation by a magnetic stirrer and is cooled with a salt/ice bath held at −10° C. The effluent is filtered and distilled at room temperature (23° C.) to recover carbamoyl chloride and excess isocyanic acid in toluene which are recycled with isocyanic acid make-up added at a rate of 2 moles per mole of DIPEB charged.

The reactor is initially charged as in Example I with HCl, isocyanic acid, p-DIPEB and the zinc etherate. Effluent withdrawal is commenced after 5 minutes and recycle of distillate and charging of fresh DIPEB and isocyanaic acid are then commenced at rates designed to provide a 5 minute average residence time in the reactor which is held at 0° C. p-DIPEB, p-TMXDI and p-TMI are recovered by fractional distillation at 25 mm. Hg of the residue after the distillation of the recycle stream, and the recovered p-DIPEB and p-TMI are recycled with the fresh DIPEB charge.

EXAMPLE IX 0.365 grams of dry hydrogen chloride (0.010 mole) was introduced into a solution of 0.43 grams of isocyanic acid (0.010 mole) in 3.44 grams of toluene at 0° under a nitrogen atmosphere. 1.18 gram of α-methylstyrene (0.010 mole) was added to the resultant carbamoyl chloride solution over a period of ten minutes while maintaining the temperature at 0° C. After fifteen minutes, cumyl chloride was present in 75% yield. 11.5 ml of 20.4% isocyanic acid in toluene (0.050 mole) was then added at 0° C. followed by addition of 0.50 ml of 1 M zinc chloride (0.00050 mole) in diisobutyl ketone over a period of 2 minutes at 0° C. After 5 minutes, cumyl isocyanate (b.p 50° C./1 mm was formed in 75% yield based α-methylstyrene.

EXAMPLE X 2.08 grams of 2,6-diisopropenylnaphthalene (0.011 mole) was added to a suspension of 1.749 gram of carbamoyl chloride (0.022 mole) in toluene over a period of ten minutes at 0° C. with stirring to give 2,6-bis (1-chloro-1-methylethyl) naphthalene which was used in the next step without isolation. Further treatment with isocyanic acid and zinc chloride as in Example I gave 2,6-bis (1-isocyanato-1-methylethyl) naphthalene in 78% yield based on 2,6-diisopropenylnaphthalene. After recrystallization from hexane the diisocyanate melted at 85°–87° C.

We claim:

1. A process for the production of tertiary benzyl isocyanates which comprises reacting a vinyl aromatic compound of the formula:

in which:
- $R_1$ is an alkylidene group having from 1 to 3 carbon atoms,
- $R_2$ is an alkyl group having from 1 to 3 carbon atoms, and
- $R_3$ is a phenyl, biphenyl or naphthyl group or a substituted phenyl, biphenyl or naphthyl group having substituents selected from halogen atoms, methyl and methoxy groups and substituents of the formula:

with a carbamoyl halide in a solvent for said aromatic compound, carbamoyl halide, isocyanic acid and reaction products thereof to produce the corresponding aromatic halide and reacting said aromatic halide in said solution with isocyanic acid in sufficient excess to form the corresponding aromatic isocyanate and carbamoyl halide.

2. A process according to claim 1 in which said reaction of said aromatic halide and isocyanic acid is carried out in the presence of a catalyst effective to promote the reaction of said aromatic halide and isocyanic acid to form said aromatic isocyanate.

3. A process according to claim 2 in which the catalyst is zinc chloride.

4. A process according to claim 1, 2 or 3 in which the solvent is toluene.

5. A process according to claim 1, 2 or 3 in which the vinyl aromatic compound is a diisopropenyl benzene.

6. A process according to claim 1, 2 or 3 in which the reaction temperature is between −10° and 10° C.

7. A process according to claim 1, 2 or 3 in which the carbamoyl halide is carbamoyl chloride.

8. A process according to claim 1, 2 or 3 in which the carbamoyl halide is carbamoyl bromide.

9. A process according to claim 1, 2 or 3 in which carbamoyl halide and excess isocyanic acid are recovered from the reaction mixture after formation of said isocyanate.

10. A process according to claim 1, 2 or 3 in which the vinyl aromatic compound is α-methylstyrene.

11. A process according to claim 1, 2 or 3 in which the vinyl aromatic is diisopropenylnaphthalene.

* * * * *